United States Patent [19]

Harada et al.

[11] Patent Number: 4,704,471
[45] Date of Patent: Nov. 3, 1987

[54] PROCESS FOR PRODUCING DL-PHENYLALANINE

[75] Inventors: Tuneo Harada, Shin-nanyo; Kiyotaka Oyama, Hikari, both of Japan

[73] Assignee: Toyo Soda Manufacturing Co., Ltd., Shin-nanyo, Japan

[21] Appl. No.: 854,709

[22] Filed: Apr. 23, 1986

Related U.S. Application Data

[63] Continuation of Ser. No. 660,368, Oct. 12, 1984, abandoned.

[30] Foreign Application Priority Data

Oct. 13, 1983 [JP] Japan .................. 58-189859

[51] Int. Cl.$^4$ .............................. C07C 99/00
[52] U.S. Cl. .................................. 562/443
[58] Field of Search ........................ 562/443

[56] References Cited

U.S. PATENT DOCUMENTS 2,109,929 3/1938 Rigby .................... 562/443
3,642,887 2/1972 Jackisch ................ 562/443

FOREIGN PATENT DOCUMENTS 989305 1/1963 United Kingdom .

OTHER PUBLICATIONS

Cheronis et al., J. Org. Chem., vol. 6, pp. 349–375 (1941).
Chadwick et al., J.A.C.S., vol. 63, pp. 2427–2431 (1941).
Zhur. Obshcei Khim. 28, pp. 227–230 (1958).
Proc. Chem. Soc. (Mar. 1962), pp. 117–118.
Chem. Abstracts, vol. 52, No. 15, 8/10/85, A. M. Yurkevich et al., col. 12797, Abstract No. 12797-e-h & Zhur. Obshchei Khim. 28, pp. 227–230 (1958).
Chem. Abstracts, vol. 60, No. 12, 6/12/64, R. Filler et al., col. 14347, Abstract No. 14347e-g & Proc. Chem. Soc. (Mar. 1962), pp. 117–118.

Primary Examiner—James H. Reamer
Attorney, Agent, or Firm—Oblon, Fisher, Spivak, McClelland, & Maier

[57] ABSTRACT

A process for producing DL-phenylalanine by reacting an α-halogeno-β-phenylpropionic acid represented by the general formula:

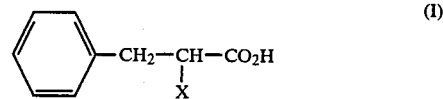

(I)

where X is a halogen atom, or its salt, with ammonia, characterized in that the reaction is conducted while supplying the α-halogeno-β-phenylpropionic acid or its salt into aqueous ammonia charged in a reactor in advance.

11 Claims, No Drawings

PROCESS FOR PRODUCING DL-PHENYLALANINE

This application is a continuation of application Ser. No. 660,368, filed Oct. 12, 1984 which is now abandoned.

FIELD OF THE INVENTION

The present invention relates to a process for producing DL-phenylalanine. More particularly, the present invention relates to a process for producing DL-phenylalanine by reacting an α-halogeno-β-phenylpropionic acid with ammonia.

DISCUSSION OF THE BACKGROUND

Heretofore, as a method for producing DL-phenylalanine from an α-halogeno-β-phenylpropionic acid, there has been known a method in which aqueous ammonia containing the α-halogeno-β-phenylpropionic acid is reacted in an autoclave at room temperature or under heating (C. S. Marvel, Org. Synth, Coll. Vol. 3, p705 (1955); A. M. Yurkevich et al., Zhur. Obshchei Khim. 28, 227 (1958)).

However, according to this method, if the reaction is conducted under heating, the yield of DL-phenylalanine is as low as from 40 to 60%, and if the reaction is conducted at room temperature, it takes about 1 week until the reaction is complete. Neither case is practical.

On the other hand, it is also known to conduct the reaction by using liquid ammonia in an autoclave at room temperature for a long period of time (R. Filler et al., Proc. Chem. Soc. 1962, 117; Can. J. Chem., 45, 325). However, the recovery of liquid ammonia is not easy, and thus the process has a problem from the industrial point of view.

The present inventors have conducted extensive researches for the process for producing DL-phenylalanine from an α-halogeno-β-phenylpropionic acid, and have found that the higher the molar ratio of ammonia to the α-halogeno-β-phenylpropionic acid in the reaction solution is, the higher the yield of DL-phenylalanine becomes. However, this process requires ammonia in great excess, and it has been found that in order to attain a good yield, e.g. about 80%, ammonia is required to be employed in an amount as much as about 40 times the stoichiometric amount. Thus, this process has difficulties in the volume efficiency of the reactor and the recovery of ammonia.

From further researches, the present inventors have found that when the reaction is conducted while supplying the α-halogeno-β-phenylpropionic acid into a solution containing ammonia charged in the reactor in advance, it is possible to produce DL-phenylalanine in good yield even if the molar ratio of ammonia to the α-halogeno-β-phenylpropionic acid is substantially lower than that in the conventional techniques. The present invention has been accomplished based on this discovery.

SUMMARY OF THE INVENTION

Namely, the present invention provides a process for producing DL-phenylalanine by reacting an α-halogeno-β-phenylpropionic acid represented by the general formula:

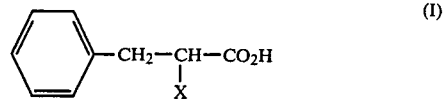

where X is a halogen atom, or its salt, with ammonia, characterized in that the reaction is conducted while supplying the α-halogeno-β-phenylpropionic acid or its salt into aqueous ammonia charged in a reactor in advance.

DETAILED DESCRIPTION OF THE PREFERRED EMBODIMENTS

Now, the present invention will be described in detail with reference to the preferred embodiments.

As the halogen atom in the α-halogeno-β-phenylpropionic acid, i.e. as X in the above general formula I, there may be mentioned chlorine, bromine and iodine.

The reaction of the present invention is conducted by adding the α-halogeno-β-phenylpropionic acid into a solution containing ammonia charged in the reactor in advance. In this case, the α-halogeno-β-phenylpropionic acid may be used as it is, or may be used in the form of a solution as dissolved in a hydrophilic organic solvent such as an alcohol. Further, an aqueous solution of its salt with an alkali metal or with ammonia may suitably be used. Particularly preferred is a method wherein the α-halogeno-β-phenylpropionic acid is used as it is, or in the form of an aqueous solution of its ammonium salt.

With respect to the supplying rate of the α-halogeno-β-phenylpropionic acid or its salt, the greater the molar ratio of ammonia to the α-halogeno-β-phenylpropionic acid is, smaller the by-products become and the higher the yield of DL-phenylalanine becomes. Accordingly, the supplying rate is preferably comparable with the conversion rate of the α-halogeno-β-phenylpropionic acid to DL-phenylalanine. The actual conversion rate varies depending upon the concentration of ammonia, the reaction temperature, the reaction pressure and the presence or absence, or the type of the hydrophilic organic solvent, and can not simply be set. However, the conversion rate can readily be measured by analyzing the reaction solution under the optional reaction condition. The ratio of the supplying rate to the conversion rate is usually from 0.01 to 2, preferably from 0.1 to 2, more preferably from 0.5 to 1. The supply may be conducted continuously or intermittently.

The amount of ammonia charged in the reactor in advance is the amount necessary for neutralizing the carboxylic acid of the α-halogeno-β-phenylpropionic acid and hydrohalogenic acid liberated by the reaction and for substituting the α-halogen group as the reaction reagent, i.e. at least 3 mols, preferably at least 5 mols, relative to 1 mol of the α-halogeno-β-phenylpropionic acid. The upper limit is not technically limited. However, it is not economically practical to use it too much, e.g. as much as 100 times the stoichiometric amount.

In the case where the α-halogeno-β-phenylpropionic acid is supplied in the form of an aqueous solution of its ammonium salt, the amount of ammonia charged in the reactor in advance is the above-mentioned amount of ammonia less the amount of ammonia brought in by the ammonium salt. The concentration of aqueous ammonia charged in the reactor in advance is not critical. However, if the concentration is too low, the reaction rate tends to be slow. On the other hand, if concentration is too high, the reactor and the recovery system for ammonia are required to be of a high pressure type. Either case may be disadvantageous. Thus, the concentration of ammonia is usually from about 10 to about 60% by weight, preferably from about 20 to about 40% by weight, more preferably from about 25 to about 30% by weight.

A hydrophilic organic solvent such as an alcohol may be incorporated in an amount which does not adversely affect the reaction.

The reaction is usually conducted in an autoclave under pressure of aqueous ammonia at the temperature at that time. However, the reaction may be conducted in the presence of an inert gas such as nitrogen gas which does not take part in the reaction.

The reaction pressure is usually from about 1 to about 50 atm., preferably from about 3 to about 30 atm., more preferably from about 5 to about 20 atm.

If the reaction temperature is too low, the reaction rate tends to be low, and if the temperature is too high, side reactions are likely to take place. Accordingly, the reaction temperature is usually from about 30° to about 200° C., preferably from about 50° to about 150° C., more preferably from about 70° to about 120° C.

The reaction time may vary depending upon the reaction temperature, the reaction pressure, the concentration of ammonia and the supplying rate of the α-halogeno-β-phenylpropionic acid, and thus optionally be set. However, it is usually from about 0.5 to about 48 hours, preferably from about 2 to about 24 hours, more preferably from about 5 to about 15 hours.

After the completion of the reaction, the excess amount of ammonia is recovered by distillation. The residue is treated by a conventional method such as concentration, cooling or isoelectric point precipitation, whereby crystals of DL-phenylalanine are precipitated and isolated.

According to the process of the present invention, DL-phenylalanine can readily be obtained in good yield. Further, in the present invention, ammonia is used in a smaller amount. Thus, the process of the present invention has advantages such that the volume efficiency of the reactor is high, and the installation cost for the ammonia recovery step can be reduced.

Now, the present invention will be described in further detail with reference to examples. However, it should be understood that the present invention is by no means restricted by these specific examples.

EXAMPLE 1

Into an autoclave having a capacity of 1000 ml, 395 g (6.5 mols) of 28 wt.% aqueous ammonia was charged and heated to 100° C. To this solution, a solution obtained by dissolving 92.3 g (0.5 mol) of α-chloro-β-phenylpropionic acid in 60 ml of water and 60 g (1 mol) of 28 wt.% of aqueous ammonia, was continuously supplied by a pump over a period of 8 hours. After the completion of the supply, the reaction mixture was further reacted for 2 hours at the same temperature. Then, the reaction solution was analyzed by high speed liquid chromatography, whereby it was found that DL-phenylalanine had been formed in a yield of 96%. Further, from the reaction solution, the excess ammonia was removed, and crude crystals of DL-phenylalanine were obtained by isoelectric point precipitation.

COMPARATIVE EXAMPLE 1

Into an autoclave having a capacity of 1000 ml, 92.3 g (0.5 mol) of α-chloro-β-phenylpropionic acid and 455 g (7.5 mols) of 28 wt.% aqueous ammonia were charged, and reacted at 100° C. for 10 hours under heating. The reaction solution was analyzed by high speed liquid chromatography, whereby it was found that DL-phenylalanine formed in a yield of 61%.

EXAMPLE 2

The reaction was conducted in the same manner as in Example 1 except that in Example 1, the amount of 28 wt.% aqueous ammonia initially charged, was changed to 546 g (9 mols), whereby it was found that DL-phenylalanine formed in a yield of 84%.

EXAMPLE 3

Into an autoclave having a capacity of 1000 ml, 510 g (8.4 mols) of 28 wt.% aqueous ammonia was fed and heated to 100° C. To this solution, a solution obtained by dissolving 55.4 g (0.3 mol) of α-chloro-β-phenylpropionic acid in 36 ml of water and 36 g (0.6 mol) of 28 wt.% aqueous ammonia, was continuously supplied by a pump over a period of 8 hours. After the completion of the supply, the reaction mixture was further reacted for 2 hours at the same temperature. Then, the reaction solution was analyzed by high speed liquid chromatography, whereby it was found that DL-phenylalanine formed in a yield of 87%.

EXAMPLE 4

Into an autoclave having a capacity of 1000 ml, 170 g (10 mols) of liquid ammonia and 245 g of distilled water were charged and heated to 80° C. To this solution, 92.3 g (0.5 mol) of α-chloro-β-phenylpropionic acid melted at 60° C., was supplied over a period of about 13 hours. After the completion of the supply, the reaction was further continued for about 3 hours at 80° C. Then, the product was analyzed by high speed liquid chromatography, whereby it was found that DL-phenylalanine formed in a yield of 84%.

EXAMPLE 5

The reaction was conducted in the same manner as in Example 3 except that in Example 3, 68.7 g (0.3 mol) of α-bromo-β-phenylpropionic acid was used instead of the α-chloro-β-phenylpropionic acid, whereby it was found that DL-phenylalanine fomred in a yield of 86%.

We claim:

1. A process for producing DL-phenylalanine by reacting an α-halogeno-β-phenylpropionic acid of the formula

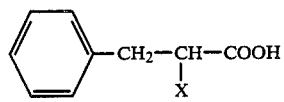

wherein X is a halogen atom, or its salt, with ammonia, said process comprising conducting the reaction by supplying the said α-halogeno-β-phenylpropionic acid or its salt to a reactor charged with aqueous ammonia over a period of time of at least 30 minutes, wherein the said reaction is conducted at a temperature of from 50° to 150° C.

2. The process according to claim 1, wherein the α-halogeno-β-phenylpropionic acid is supplied continuously or intermittently into the aqueous ammonia.

3. The process according to claim 1, wherein the α-halogeno-β-phenylpropionic acid is supplied as it is, or as an aqueous solution of its ammonium salt.

4. The process of claim 1, wherein X is chlorine, bromine or iodine.

5. The process of claim 1, wherein the α-halogeno-β-phenylpropionic acid is used in the form of a solution, wherein the α-halogeno-β-phenylpropionic acid is dissolved in a hydrophilic organic solvent.

6. The process of claim 5, wherein the hydrophilic organic solid comprises an alcohol.

7. The process of claim 1, wherein the α-halogeno-β-phenylpropionic acid is used neat.

8. The process of claim 1, wherein the α-halogeno-β-phenylpropionic acid is used in the form of an aqueous solution of its ammonium salt.

9. The process of claim 1, wherein the amount of ammonia charged in the reactor is at least 3 moles of ammonia relative to each 1 mole of the α-halogeno-β-phenylpropionic acid used.

10. The process of claim 1, wherein the amount of ammonia charged in the reactor is at least 5 moles of ammonia relative to each 1 mole of the α-halogeno-β-phenyl propionic acid used.

11. The process of claim 1, wherein the said aqueous ammonia has a concentration of from about 10 to 60% by weight.

* * * * *